United States Patent [19]

Konno et al.

[11] Patent Number: 4,816,064
[45] Date of Patent: Mar. 28, 1989

[54] TRIAZINE DERIVATIVES, HERBICIDAL COMPOSITION CONTAINING THEM, AND METHOD OF CONTROLLING GROWTH OF UNDESIRED VEGETATION BY USING SAME

[75] Inventors: Kazuhiko Konno; Kouichi Araki; Norio Sasaki; Keiji Endo, all of Ami; Mitsuru Hikido, Tokyo; Kiyoshi Sugaya, Ami, all of Japan

[73] Assignee: Mitsubishi Petrochemical Co., Ltd., Tokyo, Japan

[21] Appl. No.: 932,527

[22] Filed: Nov. 20, 1986

[30] Foreign Application Priority Data

Nov. 26, 1985 [JP] Japan .................. 60-263783

[51] Int. Cl.⁴ .................. A01N 43/70; C07D 251/52
[52] U.S. Cl. .................. 71/93; 544/208; 544/204; 544/210
[58] Field of Search .................. 71/93; 544/208, 204, 544/210

[56] References Cited

U.S. PATENT DOCUMENTS

| | | | |
|---|---|---|---|
| 3,128,272 | 4/1964 | Wear et al. | 544/204 |
| 4,459,151 | 7/1984 | Kuhle | 71/93 |
| 4,480,101 | 10/1984 | Meyer | 544/320 |
| 4,540,782 | 9/1985 | Meyer | 544/194 |
| 4,648,898 | 3/1987 | Hayase et al. | 71/93 |

*Primary Examiner*—John M. Ford
*Attorney, Agent, or Firm*—Sherman & Shalloway

[57] ABSTRACT

A 1,3,5-triazine derivative represented by the following formula (I)

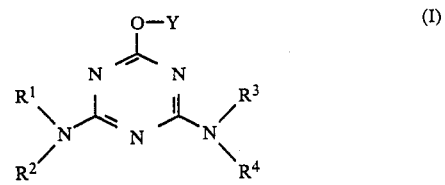

wherein $R^1$, $R^2$, $R^3$ and $R^4$, independently from each other, represent a hydrogen atom or a group selected from the class consisting of linear or branched $C_1$–$C_6$ alkyl groups, $C_2$–$C_6$ alkenyl groups, $C_2$–$C_6$ alkynyl groups, $C_1$–$C_6$ alkyl groups substituted by $C_1$–$C_6$ alkoxy or alkylthio, $C_3$–$C_6$ cycloalkyl groups, a phenyl group unsubstituted or substituted by a substituent selected from halogen, nitro, cyano, lower alkyl, lower alkoxy, lower alkylthio and fluoro-substituted lower alkyl, $C_7$–$C_9$ aralkyl groups unsubstituted or substituted by a substituent selected from halogen, nitro, cyano, lower alkyl, lower alkoxy, lower alkylthio and fluoro-substituted lower alkyl, and alkoxycarbonylmethyl groups having 1 to 6 carbon atoms in the alkoxy moiety; and Y represents a fluoro-substituted $C_1$–$C_3$ alkyl group and a herbicidal use thereof.

10 Claims, No Drawings

TRIAZINE DERIVATIVES, HERBICIDAL COMPOSITION CONTAINING THEM, AND METHOD OF CONTROLLING GROWTH OF UNDESIRED VEGETATION BY USING SAME

This invention relates to novel triazine derivatives not described in the prior known literature, herbicidal compositions comprising them as active ingredients, and a method of controlling the growth of undesired vegetation by using these novel triazine derivatives. The novel compounds show good selectivity such that they have excellent herbicidal activity against undesired vegetation such as weeds and reduced phytotoxicity to useful cultivated plants such as crops. The invention also pertains to a process for producing these novel compounds.

More specifically, this invention relates to a 1,3,5-triazine derivative represented by the following formula (I)

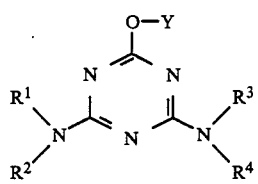

(I)

wherein $R^1$, $R^2$, $R^3$ and $R^4$, independently from each other, represent a hydrogen atom or a group selected from the class consisting of linear or branched $C_1$–$C_6$ alkyl groups, $C_2$–$C_6$ alkenyl groups, $C_2$–$C_6$ alkynyl groups, $C_1$–$C_6$ alkyl groups substituted by $C_1$–$C_6$ alkoxy or alkylthio, $C_3$–$C_6$ cycloalkyl groups, a phenyl group unsubstituted or substituted by a substituent selected from halogen, nitro, cyano, lower alkyl, lower alkoxy, lower alkylthio and fluoro-substituted lower alkyl, $C_7$–$C_9$ aralkyl groups unsubstituted or substituted by a substituent selected from halogen, nitro, cyano, lower alkyl, lower alkoxy, lower alkylthio and fluoro-substituted lower alkyl, and alkoxycarbonylmethyl groups having 1 to 6 carbon atoms in the alkoxy moiety; and Y represents a fluoro-substituted $C_1$–$C_3$ alkyl group.

The invention also pertains to a herbicidal composition comprising the compound of formula (I) as an active ingredient, a process for producing the compound of formula (I), and a method of controlling the growth of undesired vegetation by using the compound of formula (I).

Some 1,3,5-triazine-type compounds having herbicidal or plant growth controlling activity have previously been known. For example, Swiss Pat. No. 329,277 discloses 2-chloro-4,6-bis(ethylamino)-1,3,5-triazine (simazine), and 2-chloro-4-ethylamino-6-isopropylamino-1,3,5-triazine (atrazine). Swiss Pat. No. 337,019 discloses 2-ethylamino-4-methylthio-6-isopropyl-1,3,5-triazine (ametryn) and 2,4-bis(ethylamino)-6-methylthio-1,3,5-triazine (simetryn). These patents, however, quite fail to describe or suggest compounds which can embrace the triazine derivatives of formula (I) of this invention having the group —O—Y. Known 1,3,5-triazine herbicides such as those disclosed in the above-cited patents are widely used in upland farms and paddies against dicotyledonous plants by soil or foliar treatment before or after emergence. Their selectivity on cultivated plants and herbicidal activity against weeds are not entirely satisfactory, and are desired to be improved further.

Japanese Laid-Open Patent Publication No. 47471/1986 laid open on Mar. 7, 1986 (corresponding to GB No. 2,163,161A published on 19th Feb., 1986), which was published after the priority date of the present application, discloses 2,4-diamino-6-difluoromethylthio-1,3,5-triazine derivatives of the following formula (a) which are useful as a herbicide.

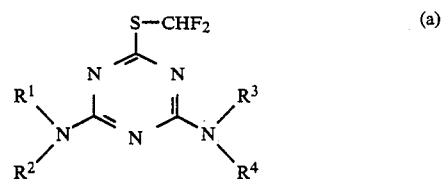

(a)

wherein $R^1$, $R^2$, $R^3$ and $R^4$ are each independently hydrogen, an aliphatic hydrocarbon residue, lower alkoxy-(lower alkyl), cyano-(lower alkyl), or aryl-(lower alkyl), or ($R^1$ and $R^2$) or ($R^3$ and $R^4$) taken together form lower alkylene.

The formula (a) given in this prior application cannot encompass the compound of formula (I) having —O—Y at the 6-position, and this prior application does not at all describe the excellent herbicidal activity of the compounds of formula (I) given above.

The present inventors have undertaken research and development work on 1,3,5-triazine derivatives having improved herbicidal properties. Consequently, they have found that the triazine derivatives of formula (I) not described in the prior known literature can be easily synthesized, and have succeeded in synthesizing these compounds.

The present inventors have further studied the biological properties of the compounds of formula (I) on plants, and found that the compounds of formula (I) have biological properties useful for controlling the growth of undesired vegetation; that they have particularly good herbicidal activity against weeds and good selectivity on cultivated plants; and that they have a broad herbicidal spectrum including upland farm weeds and paddy weeds, are useful for controlling these weeds, and do not substantially show phytotoxicity to cultivated plants when applied in amounts required to kill the weeds.

It is an object of this invention to provide novel triazine derivatives represented by formula (I).

Another object of this invention is to provide a herbicidal composition comprising a compound of formula (I) as an active ingredient.

The above and other objects and advantages of this invention will become more apparent from the following description.

The novel triazine derivatives of this invention are represented by the following formula (I)

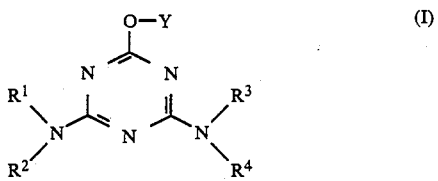

(I)

wherein $R^1$, $R^2$, $R^3$, $R^4$ and Y are as defined above.

Examples of the definition of these symbols in formula (I) are given below.

Examples of the linear or branched $C_1$–$C_6$ alkyl groups are methyl, ethyl, n-propyl, iso-propyl, n-butyl, sec-butyl, iso-butyl, tert-butyl, n-pentyl, tert-pentyl, 1-ethylpropyl, n-hexyl and 1-methylpentyl groups.

Examples of the $C_2$–$C_6$ alkenyl groups include vinyl, allyl, 1-propenyl, isopropenyl, 1-butenyl, 2-butenyl, 3-butenyl, 1-methyl-2-propenyl, 1,3-butadienyl, and 1,1-dimethyl-2-propenyl groups.

Examples of the $C_2$–$C_6$ alkynyl groups are ethynyl, 2-propynyl, 1-butynyl, 2-butynyl, 1-methyl-2-propynyl and 1,1-dimethyl-2-propynyl groups.

In the $C_1$–$C_6$ alkyl groups substituted by $C_1$–$C_6$ alkoxy or alkylthio, examples of the substituent $C_1$–$C_6$ alkoxy are methoxy, ethoxy, n-propoxy, iso-propoxy, n-butoxy, n-pentoxy and n-hexyloxy groups, and examples of the substituent $C_1$–$C_6$ alkylthio are methylthio, ethylthio, n-propylthio, iso-propylthio, n-butylthio, n-pentylthio and n-hexylthio groups. The alkyl moiety of the $C_1$–$C_6$ alkyl groups substituted by these substituents may be the same linear alkyl groups as exemplified above for the $C_1$–$C_6$ linear or branched alkyl groups.

Examples of the $C_3$–$C_6$ cycloalkyl group are cyclopropyl, cyclobutyl, cyclopentyl and cyclohexyl groups.

The substituent on the phenyl group in formula (I) includes, for example, fluorine, chlorine, bromine, a methyl group, an ethyl group, a methoxy group, an ethoxy group, a methylthio group, a trifluoromethyl group, a nitro group, and a cyano group.

The same substituents as given above for the phenyl group may be cited as examples of the substituent in the substituted $C_7$–$C_9$ aralkyl groups. Examples of the $C_7$–$C_9$ aralkyl groups are benzyl, 1-phenethyl, 2-phenethyl and cumyl groups.

Examples of $C_1$–$C_6$ alkoxy in the alkoxycarbonylmethyl groups having 1 to 6 carbon atoms in the alkoxy moiety may be the same alkoxy groups as exemplified above for $C_1$–$C_6$ alkoxy groups substituted by $C_1$–$C_6$ alkoxy or alkylthio.

In the $C_1$–$C_6$ alkyl groups substituted by $C_1$–$C_6$ alkoxy or alkylthio, the alkyl groups may be mono- or poly-substituted, preferably mono- or di-substituted. The optionally substituted phenyl group and the optionally substituted aralkyl group in formula (I) may also be mono- or poly-substituted, preferably mono-, di- or tri-substituted.

Examples of the alkyl group in the fluoro-substituted $C_1$–$C_3$ alkyl group represented by Y in formula (I) include methyl, ethyl, n-propyl and iso-propyl groups. These alkyl groups are substituted by one or more fluorine atoms. Thus, examples of the fluoro-substituted alkyl groups may include fluoromethyl, difluoromethyl, trifluoromethyl, 2-fluoroethyl, 1,1,2,2-tetrafluoroethyl, 2,2,2-trifluoroethyl, 2,2,3,3-tetrafluoropropyl and 2,2,3,3,3-pentafluoropropyl groups.

Preferred compounds of formula (I) are those in which —O—Y is —OCHF$_2$, and

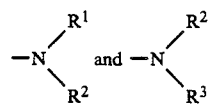

are —NHR$^1$ and —NHR$^3$ respectively and are represented by the following formula (I)'. Especially preferably, in formula (I)', R$^1$ and R$^3$, independently from each other, are selected from linear or branched C1–C4 alkyl groups and C3–C6 cycloalkyl groups (particularly a cyclopropyl group).

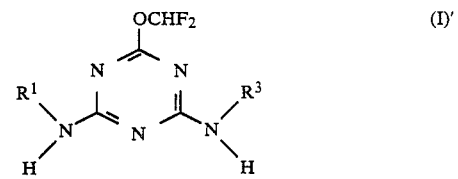

wherein R$^1$ and R$^3$, independently from each other, represent a group selected from the class consisting of linear or branched $C_1$–$C_6$ alkyl groups, $C_2$–$C_6$ alkenyl groups, $C_1$–$C_6$ alkyl groups substituted by $C_1$–$C_6$ alkoxy, $C_3$–$C_6$ cycloalkyl groups, a phenyl group unsubstituted or substituted by a substituent selected from halogen, nitro, cyano, lower alkyl, lower alkoxy, lower alkylthio and fluoro-substituted lower alkyl, and $C_7$–$C_9$ aralkyl groups unsubstituted or substituted by a substituent selected from halogen, nitro, cyano, lower alkyl, lower alkoxy, lower alkylthio and fluoro-substituted lower alkyl.

The compound of formula (I) in accordance with this invention can be easily produced, for example, by reacting a 1,3,5-triazin-2-ol of formula (II) in which R$^1$, R$^2$, R$^3$ and R$^4$ are as defined hereinabove with a compound of formula (III) in which Y is as defined and Hal represents a halogen such as chlorine, bromine or iodine, in the presence of a base.

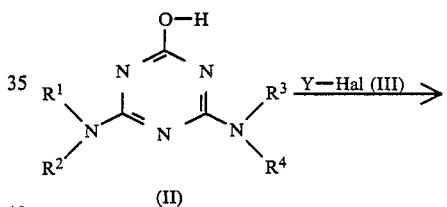

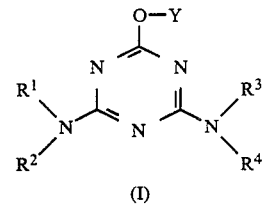

In the production of the compound of formula (I) in accordance with the above embodiment, the reaction is conveniently carried out in an inert solvent or a mixture of inert solvents. Examples of suitable solvents are ethers such as dioxane, tetrahydrofuran, ethylene glycol dimethyl ether and diethylene glycol dimethyl ether, alcohols, such as methanol and ethanol, ketones such as acetone and ethyl methyl ketone, acetonitrile, dimethylformamide, and dimethyl sulfoxide. Examples of suitable bases for use in the above reaction include sodium hydride, sodium hydroxide, potassium hydroxide, potassium carbonate, and sodium hydrogen carbonate. The base may be added in the form of an aqueous solution if it is suitable. The reaction temperature can be properly selected, and may, for example, be 0° C. to the boiling point of the solvent. The reaction time can be varied suitably depending upon the reaction temperature, the type of the reagent, etc., and may, for example, be about 10 minutes to about 20 hours. After the reaction, the reaction mixture may be treated in a customary manner, for example by column chromatography, distillation or recrystallization to purify the desired product. The starting compound of general formula (II) can be obtained by a known method or a method similar to it.

The compounds of formula (I) provided by this invention are useful for weed control with a broad herbicidal spectrum, and do not substantially cause phytotoxicity to useful cultivated plants when applied in amounts required for weed control.

According to this invention, there is provided a herbicide comprising the 1,3,5-triazine derivative of formula (I), preferably formula (I)′, as an active ingredient.

The present invention thus provides a herbicidal composition comprising a herbicidally effective amount of a 1,3,5-triazine derivative of formula (I) or (I)′ as an active ingredient and an agriculturally acceptable diluent or carrier.

The agriculturally acceptable diluent and carrier that can be used to prepare the herbicidal composition are well known in the art and known diluents and carriers can be used in this invention. Examples of such diluent or carrier include solid carriers or diluents for example clays typified by clays of the kaolinite, montmorillonite and attapulgite groups; inorganic substances such as talc, mica, pyrophyllite, pumice, vermiculite, gypsum, calcium carbonate, diatomaceous earth, magnesium lime, phosphorus lime, zeolite and silicic anhydride; vegetable organic substances such as soybean meal, wheat flour and crystalline cellulose; synthetic or natural polymeric compounds such as petroleum resins, polyvinyl chloride, polyalkylene glycols, ketone resins, ester gum and copal gum; urea, and liquid carriers or diluents which are solvents or non-solvents capable of dispersing or dissolving the compounds of this invention by the aid of adjuvants, for example paraffinic or naphthenic hydrocarbons such as kerosene, mineral oils, spindle oils, and white oils; aromatic hydrocarbons such as benzene, toluene, xylene, ethylbenzene, cumene and methylnaphthalene; chlorinated hydrocarbons such as carbon tetrachloride, chloroform, trichloroethylene, monochloro benzene and o-chlorobenzene; ethers such as dioxane and tetrahydrofuran; ketones such as acetone, methyl ethyl ketone, isobutyl ketone, cyclohexanone and isophorone; esters such as ethyl acetate, amyl acetate, ethylene glycol acetate, diethylene glycol acetate and diethyl succinate; alcohols such as methanol, n-hexanol, ethylene glycol and diethylene glycol; ether alcohols such as ethylene glycol ethyl ether, diethylene glycol ethyl ether and diethylene glycol butyl ether; dimethyl formamide; and dimethyl sulfoxide.

The herbicidal composition may be in any desired form composed of the compound of formula (I) or (I)′ and the agriculturally acceptable diluent or carrier together with adjuvants such as a solvent, an emulsifier and a sticker. Such forms and the method of preparing the herbicidal composition are well known in the art. For example, the herbicidal composition of this invention may be in the form of an emulsifiable concentrate, a liquid preparation, a wettable powder, a dust or granules. The herbicidal composition of this invention may contain about 1 to 80% by weight, based on the weight of the composition, of the compound of formula (I) or (I)′.

The compounds of formula (I) provided by this invention have a herbicidal efficacy against various weeds causing hazards to crops in upland farms in soil or foliar treatment. Examples of the weeds are broad-leaved weeds such as wild buckwheat (*Polygonum convolvulus*), smartweed (*Polygonum lapathiofolium*), common purslane (*Portulaca oleracea*), common chickweed (*Stellaria media*), lamb's quarters (*Chenopodium album*), redroot pigweed (*Amaranthus retroflexus*), Charlock (*Brassica kaber*), shepherd's purse (*Capsella bursa-pastoris*), hempsesbania (*Sesbania exaltata*), velvetleaf (*Abutilan theophrasti*), prickly sida (*Sida spinosa*), field pansy, wild carrot (*Daucus carota*), ivyleaf morningglory (*Pharbitis hederacea*), tall morningglory (*Pharbitis purpurea*), field bindweed (*Convolvulus arvensis*), red deadnettle (*Lamium purpureum*), deadnettle (*Lamium amplexicaule*), Jimsonweed (*Datura stramonium*), black nightshade (*Solanum nigrum*), birdseye speedwell (*Veronica persica*), ivyleaf speedwell (*Veronica hederafolia*), cocklebur (*Xanthium strumarium*), mayweed (*Tritleurospermum meritimum*), and corn marigold (*Chrysanthemum segetum*); gramineous weeds such as barnyard grass (*Echinochloa crus-galli*), green foxtail (*Setaria viridis*), large crabgrass (*Digitaria sanguinalis*), anual bluegrass (*Poa annua*), black grass (*Alopeculus myosuroides*), wild oat(*Avena fatua*), Johnsongrass (*Sorghum halepens*), quack grass (*Agropyron repens*) and downy brome (*Bromus tectorum*); cyperaceous weedssuch as rice flatsedge (*Cyperus iria*) and purple nutsedge (*Cyperus rotundus*). Some of the compounds of this invention do not cause phytotoxicity which causes a significant injury to main crops such as corn, wheat, rice, soybean, cotton and sunflower. Furthermore, some of the compounds of this invention show an excellent herbicidal effect against weeds causing various hazards to paddies, for example gramineous weeds such as barnyard grass and *Echinochloa oryziloca*, broad-leaved weeds such as common falsepimpernel (*Lindernia pyxidaria*), *Rotala indica* and American waterwort (*Elatine triandra*), and cyperaceous weeds such as umbrella plant (*Cyperus difformis*), bulrush (*Scirpus juncoides*), spikerush (*Eleocharis acicularis*) and *Cyperus serotinus*, and other paddy weeds such as monochoria (*Monochoria vaginalis*) and narrowleaf waterplantain (*Alisma canaliculatum*) without causing any significant phytotoxicity to rice plants.

Accordingly, the compound of this invention or the herbicidal composition containing it as an active ingredient can be used as a herbicide in paddies, upland farms, orchards, pastures, lawns, forests and non-agricultural lands.

As shown by Test Examples to be given hereinafter, the novel 1,3,5-triazine derivatives of this invention show excellent activity as an active ingredient of a herbicide, and have selective herbicidal activity such that they kill gramineous and broad-leaved weeds witout causing injury to crops such as corn, soybean, cotton, sugar beet, sunflower and rice.

According to this invention, there is also provided a method of controlling the growth of undesired vegetation which comprises applying an agriculturally effective amount of at least one compound of formula (I) to the locus of such vegetation.

The compound of formula (I) may be applied as such or in the form of the herbicidal composition. The locus and time of application may be properly chosen. For example, the compound (I) of this invention may be applied to weeds which occur in paddies, upland farms, orchards, pastures, lawns, forests and non-agricultural lands before energence or at a time up to the growth stage after emergence. In particular, the compounds of this invention are safe agaunst corn, soybean, cotton, sugar beet, sunflower and rice, and can control various weeds from the time before emergence to the growth stage.

In pre-emergence application, incorporation of the active compound in the soil is as effective as treatment of the soil surface with the compound. In application in the growth stage, when weeds growing in the locus where useful plants having high sensitivity to the compound of this invention are to be controlled, it is possible to utilize a technique of applying the herbicide to the leaves and stalks of weeds growing around the useful plants or to the soil while a care is taken not to have the herbicide scattered and adhered to the leaves and stalks of the useful plants.

In a preferred mode of carrying out the method of this invention, the compound of the invention is applied before the emergence of undesired vegetation such as weeds to the soil and/or the soil surface where the undesired vegetation is likely to occur.

The rate of the compound of formula (I) to be applied can be varied properly depending upon, for example, the climatic conditions, the soil condition, the form of the herbicide, the time of application, the method of application, the type of weeds to be controlled, and the purpose of weed control. For example, the amount of the compound of formula (I) to be applied may be about 0.01 to 10 kg/hectare, preferably about 0.05 to 5 kg/hectare.

The herbicidal composition of this invention may be used in admixture or combination with agricultural chemicals such as another herbicide, an insecticide and a fungicide, a fertilizer, and soil, in which case a better effect may sometimes be expected. Examples of the other herbicides may include carbamate chemicals such as EPTC, butylate and phenisopham, amide chemicals such as alachlor, metolachlor, acetochlor, propachlor, trimexachlor, xylachlor and diphenamide, triazine chemicals such as atrazine, cyanazine, simazine, metribuzin and prometryne, dinitroaniline chemicals such as trifluralin, pendimethalin, fluochloralin, ethalfluralin and oryzalin, urea chemicals such as diuron, linuron and fluometuron, and other herbicides such as fluorochloridone, benfuresate, cinmethylin, norflurazone, tridiphane, glyphosate, bialaphos, paraquat, diquat, chlorsulfuron, sulfometuron, metsulfuron, imazaquin, imazapyr, 2,4-D, MCP, MCPP, dicamba, chloramben, clopyralide, picloram, dimethazone, acifluorfen, oxyfluorofen, lactofen, fomesafen, alloxydim, sethoxydim, diclofop, fluazifop, haloxyfop, quizalofop, fenoxaprop, mefluidide, and bentazone.

The following examples illustrate the production of the compound (I) of this invention, testing of the herbicide of this invention on plants, and the preparation of the herbicidal composition. It should be understood that the invention is not limited to these examples alone.

Production of the novel triazine derivatives of the invention are given in the following Examples. The products in these examples were identified by IR, NMR, mass spectroscopy, gas chromatography, etc.

EXAMPLE 1

Synthesis of 2-difluoromethoxy-4-ethylamino-6-isopropylamino-1,3,5-triazine:

A mixture of 200 g (1.02 moles) of 2-ethylamino-4-hydroxy-6-isopropylamino-1,3,5-triazine, 454 g (8.11 moles) of potassium hydroxide, 1150 ml of diethylene glycol dimethyl ether and 1150 ml of water was vigorously stirred, and heated to 90° C. Chlorodifluoromethane gas was blown into the reaction mixture until 2-ethylamino-4-hydroxy-6-isopropylamino-1,3,5-triazine was no longer detected by thin-layer chromatography. After the reaction, the reaction mixture was cooled to room temperature, extracted with methylene chloride. The methylene chloride layer was washed with water twice or thrice, dried over anhydrous magnesium sulfate, and filtered. The filtrate was concentrated under reduced pressure. The crude product was chromatographed on a silica gel column. The column was eluted with n-hexane/ethyl acetate (5:1) to give 58.9 g of 2-difluoromethoxy-4-ethylamino-6-isopropylamino-1,3,5-triazine.

$n_D{}^{25}$: 1.494

Mass spectrum: m/e 247.

NMR (CDCl$_3$ solvent, $\delta$): 7.43 (1H, t), 4.22 (1H, dq), 3.45 (2H, dq), 1.22 (6H, d), 1.20 (3H, t).

EXAMPLE 2

Synthesis of 2-difluoromethoxy-4,6-bis(isopropylamino)-1,3,5-triazine:

Example 1 was repeated except that a mixture of 49.9 g (0.24 mole) of 2,4-bis(isopropylamino)-6-hydroxy-1,3,5-triazine, 105.6 g (1.89 moles) of potassium hydroxide, 350 ml of diethylene glycol dimethyl ether, and 350 ml of water was used instead of the mixture used in Example 1. There was obtained 18.6 g of 2-difluoromethoxy-4,6-bis(isopropylamino)-1,3,5-triazine.

Melting point: 81°–82° C.

Mass spectrum: m/e 261

NMR (CDCl$_3$ solvent, $\delta$): 7.43 (1H, t), 4.20 (2H, d), 1.22 (12H, d).

The compounds shown in Table 1 were obtained by the same way as in Example 1 or 2.

TABLE 1

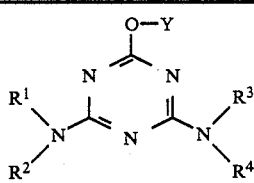

(I)

| Compd. No. | Y | R$^1$ | R$^2$ | R$^{23}$ | R$^4$ | Physical Property |
|---|---|---|---|---|---|---|
| 1 | CHF$_2$ | Me | H | cyclo-Pr | H | m.p. 96–98° C. |
| 2 | CHF$_2$ | Me | H | t-Bu | H | m.p. 87–89° C. |
| 3 | CHF$_2$ | Me | H | sec-Bu | H | m.p. 70–74° C. |
| 4 | CHF$_2$ | Me | H | iso-Bu | H | m.p. 81–83° C. |
| 5 | CHF$_2$ | Me | H | n-Bu | H | |
| 6 | CHF$_2$ | Me | H | (CH$_2$O)$_3$OMe | H | |
| 7 | CHF$_2$ | Me | H | —CHEt$_2$ | H | $n_D{}^{23}$ 1.497 |
| 8 | CHF$_2$ | Me | H | —CMeEt | H | m.p. 94–97° C. |

TABLE 1-continued $$\text{(I)}$$

Structure: triazine with O-Y at top, R$^1$R$^2$N and R$^3$R$^4$N substituents

| Compd. No. | Y | R$^1$ | R$^2$ | R$^{23}$ | R$^4$ | Physical Property |
|---|---|---|---|---|---|---|
| 9 | CHF$_2$ | Et | H | Et | H | m.p. 74–76° C. |
| 10 | CHF$_2$ | Et | H | iso-Pr | H | $n_D^{25}$ 1.494 |
| 11 | CHF$_2$ | Et | H | n-Pr | H | m.p. 80–81° C. |
| 12 | CHF$_2$ | Et | H | t-Bu | H | m.p. 97–99° C. |
| 13 | CHF$_2$ | Et | H | sec-Bu | H | m.p. 97–99° C. |
| 14 | CHF$_2$ | Et | H | Et | Et | m.p. 119–120° C. |
| 15 | CHF$_2$ | Et | H | —CH$_2$CH=CH$_2$ | H | m.p. 54–56° C. |
| 16 | CHF$_2$ | Et | H | C$_6$H$_5$ | H | m.p. 132–134° C. |
| 17 | CHF$_2$ | Et | H | —CH(CH$_3$)—C$_6$H$_5$ | H | $n_D^{23}$ 1.544 |
| 18 | CHF$_2$ | Me | H | iso-Pr | H | m.p. 78–79° C. |
| 19 | CHF$_2$ | iso-Pr | H | iso-Pr | H | m.p. 81–82° C. |
| 20 | CHF$_2$ | iso-Pr | H | n-Pr | H | m.p. 62–63° C. |
| 21 | CHF$_2$ | iso-Pr | H | cyclo-Pr | H | $N_D^{23}$ 1.506 |
| 22 | CHF$_2$ | iso-Pr | H | t-Bu | H | m.p. 111–113° C. |
| 23 | CHF$_2$ | iso-Pr | H | sec-Bu | H | $N_D^{23}$ 1.492 |
| 24 | CHF$_2$ | iso-Pr | H | iso-Bu | H | m.p. 64–67° C. |
| 25 | CHF$_2$ | iso-Pr | H | n-Bu | H | m.p. 61–64° C. |
| 26 | CHF$_2$ | iso-Pr | H | Me | Me | m.p. 107–108° C. |
| 27 | CHF$_2$ | iso-Pr | H | Et | Et | m.p. 84–85° C. |
| 28 | CHF$_2$ | iso-Pr | H | CH$_2$CH=CH$_2$ | H | $N_D^{22}$ 1.504 |
| 29 | CHF$_2$ | iso-Pr | H | (CH$_2$)$_3$OMe | H | m.p. 57–58° C. |
| 30 | CHF$_2$ | iso-Pr | H | (CH$_2$)$_2$OMe | H | m.p. 82–84° C. |
| 31 | CHF$_2$ | iso-Pr | H | (CH$_2$)$_2$OEt | H | $N_D^{23}$ 1.492 |
| 32 | CHF$_2$ | iso-Pr | H | (CH$_2$)$_3$SMe | H | $N_D^{23}$ 1.522 |
| 33 | CHF$_2$ | Me | H | n-Pr | H | m.p. 76–77° C. |
| 34 | CHF$_2$ | n-Pr | H | n-Pr | H | m.p. 78–79° C. |
| 35 | CHF$_2$ | n-Pr | H | cyclo-Pr | H | m.p. 55–56° C. |
| 36 | CHF$_2$ | n-Pr | H | t-Bu | H | m.p. 75–77° C. |
| 37 | CHF$_2$ | n-Pr | H | sec-Bu | H | $n_D^{23}$ 1.493 |
| 38 | CHF$_2$ | n-Pr | H | (CH$_2$)$_3$OMe | H | m.p. 103–104° C. |
| 39 | CHF$_2$ | Me | Me | t-Bu | H | m.p. 77–78° C. |
| 40 | CH$_2$CF$_3$ | Et | H | Et | H | m.p. 125–126° C. |
| 41 | CH$_2$CH$_2$F | Et | H | Et | H | m.p. 95–96° C. |
| 42 | CH$_2$CF$_2$CHF$_2$ | Et | H | i-Pr | H | $n_D^{23}$ 1.475 |
| 43 | CH$_2$CF$_2$CF$_3$ | Et | H | Et | H | m.p. 78–79° C. |
| 44 | CHF$_2$ | Et | H | —CHEt$_2$ | H | $n_D^{21}$ 1.495 |

TEST EXAMPLE 1

Soil treatment in a submerged condition:

Paddy soil and a chemical fertilizer were put in plastic pots having an area of 200 cm$^2$. Water was added, and these materials were well stirred. Seeds of test weeds were sown, and rice seedlings (in the 2.5 leaf-stage) which had been grown were transplanted at a rate of two stocks each consisting of two seedlings per pot.

Three days after the transplantation and sowing, a predetermined amount of each of the test compounds of this invention prepared as a wettable powder (in accordance with Formulation Example 2 given hereinafter) was applied to the pots. Thirty days after the treatment, the herbicidal effects of the test compounds on the weeds and their phytotoxicity to rice were examined, and the results are shown in Table 2.

In the table, the herbicidal effects and the degree of phytotoxicity were expressed on a scale of 6 grades represented by the following figures and symbols.

| Herbicidal effect | Herbicidal rate (%) | Degree of phytotoxicity |
|---|---|---|
| 5 | >95 | x: withered |
| 4 | 81–94 | +++: enormous injury |
| 3 | 61–80 | ++: medium injury |
| 2 | 41–60 | +: small injury |
| 1 | 21–40 | ±: slight injury |
| 0 | 0–20 | —: no action |

In Tables 2 and 3, the names of the weeds in the column of "Herbicidal effect" are shown by abbreviations as follows:

A: barnyard grass
B: bulrush
C: monochoria
D: *Rotala indica*

TABLE 2

| Compd. No. | Rate of application (kg/ha) | Herbicidal effect | | | | Phytotoxicity to rice |
|---|---|---|---|---|---|---|
| | | A | B | C | D | |
| 1 | 1 | 5 | 2 | 5 | 5 | — |
| | 0.3 | 2 | 0 | 2 | 5 | — |

TABLE 2-continued

| Compd. No. | Rate of application (kg/ha) | Herbicidal effect A | B | C | D | Phytotoxicity to rice |
|---|---|---|---|---|---|---|
| 2 | 1 | 5 | 5 | 5 | 5 | — |
|   | 0.3 | 5 | 3 | 5 | 5 | — |
| 3 | 1 | 5 | 5 | 5 | 5 | — |
|   | 0.3 | 5 | 4 | 5 | 5 | — |
| 4 | 1 | 5 | 5 | 5 | 5 | — |
|   | 0.3 | 4 | 2 | 5 | 5 | — |
| 7 | 1 | 5 | 5 | 5 | 5 | — |
|   | 0.3 | 5 | 4 | 5 | 5 | — |
| 8 | 1 | 5 | 5 | 4 | 5 | — |
|   | 0.3 | 5 | 3 | 4 | 5 | — |
| 9 | 1 | 5 | 3 | 5 | 5 | — |
|   | 0.3 | 4 | 2 | 4 | 4 | — |
| 10 | 1 | 5 | 5 | 5 | 5 | ± |
|   | 0.3 | 5 | 4 | 5 | 5 | — |
| 11 | 1 | 5 | 4 | 5 | 5 | — |
|   | 0.3 | 2 | 2 | 4 | 5 | — |
| 12 | 1 | 5 | 4 | 5 | 5 | — |
|   | 0.3 | 5 | 4 | 5 | 5 | — |
| 13 | 1 | 5 | 5 | 5 | 5 | — |
|   | 0.3 | 5 | 4 | 5 | 5 | — |
| 14 | 1 | 5 | 5 | 5 | 5 | — |
|   | 0.3 | 4 | 4 | 5 | 5 | — |
| 15 | 1 | 4 | 3 | 5 | 5 | — |
|   | 0.3 | 3 | 2 | 4 | 5 | — |
| 16 | 1 | 4 | 2 | 5 | 5 | — |
|   | 0.3 | 3 | 1 | 4 | 5 | — |
| 17 | 1 | 4 | 3 | 4 | 5 | — |
|   | 0.3 | 3 | 0 | 3 | 4 | — |
| 18 | 1 | 5 | 5 | 5 | 5 | — |
|   | 0.3 | 5 | 3 | 5 | 5 | — |
| 19 | 1 | 5 | 5 | 5 | 5 | — |
|   | 0.3 | 4 | 4 | 5 | 5 | — |
| 20 | 1 | 5 | 4 | 5 | 5 | — |
|   | 0.3 | 2 | 3 | 4 | 4 | — |
| 21 | 1 | 5 | 5 | 5 | 5 | — |
|   | 0.3 | 5 | 5 | 5 | 5 | — |
| 22 | 1 | 5 | 4 | 5 | 5 | — |
|   | 0.3 | 5 | 2 | 5 | 5 | — |
| 23 | 1 | 5 | 5 | 5 | 5 | — |
|   | 0.3 | 5 | 4 | 5 | 5 | — |
| 24 | 1 | 5 | 5 | 5 | 5 | — |
|   | 0.3 | 5 | 4 | 5 | 5 | — |
| 25 | 1 | 5 | 4 | 5 | 5 | — |
|   | 0.3 | 2 | 3 | 4 | 4 | — |
| 28 | 1 | 5 | 5 | 5 | 5 | — |
|   | 0.3 | 4 | 2 | 3 | 1 | — |
| 29 | 1 | 5 | 5 | 5 | 5 | — |
|   | 0.3 | 5 | 5 | 5 | 5 | — |
| 30 | 1 | 5 | 5 | 5 | 5 | — |
|   | 0.3 | 4 | 2 | 3 | 5 | — |
| 31 | 1 | 5 | 5 | 5 | 5 | — |
|   | 0.3 | 5 | 3 | 5 | 5 | — |
| 32 | 1 | 5 | 2 | 4 | 5 | — |
|   | 0.3 | 4 | 1 | 3 | 4 | — |
| 33 | 1 | 5 | 4 | 5 | 5 | — |
|   | 0.3 | 4 | 3 | 5 | 5 | — |
| 34 | 1 | 5 | 3 | 5 | 5 | — |
|   | 0.3 | 4 | 2 | 4 | 4 | — |
| 35 | 1 | 5 | 5 | 5 | 5 | — |
|   | 0.3 | 2 | 1 | 4 | 5 | — |
| 36 | 1 | 5 | 3 | 5 | 5 | — |
|   | 0.3 | 3 | 2 | 3 | 5 | — |
| 37 | 1 | 5 | 3 | 5 | 5 | — |
|   | 0.3 | 4 | 0 | 4 | 5 | — |
| 38 | 1 | 5 | 5 | 5 | 5 | — |
|   | 0.3 | 4 | 2 | 4 | 5 | — |
| Symetryn | 1 | 5 | 3 | 5 | 5 | + |
|   | 0.3 | 3 | 2 | 4 | 5 | — |

TEST EXAMPLE 2

Treatment in a submerged condition during the growth period:

Test Example 1 was repeated except that the treatment was carried out 10 days (when the barnyard grass was in the 1.5 leaf stage) after the sowing and transplantation. The results are shown in Table 3.

TABLE 3

| Compd. No. | Rate of application (kg/ha) | Herbicidal effect A | B | C | D | Phytotoxicity to rice |
|---|---|---|---|---|---|---|
| 1 | 1 | 5 | 4 | 5 | 5 | — |
|   | 0.3 | 4 | 2 | 5 | 5 | — |
| 2 | 1 | 5 | 5 | 5 | 5 | — |
|   | 0.3 | 4 | 5 | 5 | 5 | — |
| 3 | 1 | 5 | 5 | 5 | 5 | — |
|   | 0.3 | 5 | 5 | 5 | 5 | — |
| 4 | 1 | 5 | 5 | 5 | 5 | — |
|   | 0.3 | 4 | 2 | 5 | 5 | — |
| 7 | 1 | 5 | 5 | 5 | 5 | — |
|   | 0.3 | 5 | 4 | 5 | 5 | — |
| 8 | 1 | 4 | 4 | 5 | 5 | — |
|   | 0.3 | 4 | 3 | 5 | 5 | — |
| 9 | 1 | 5 | 5 | 5 | 5 | — |
|   | 0.3 | 5 | 2 | 5 | 4 | — |
| 10 | 1 | 5 | 5 | 5 | 5 | — |
|   | 0.3 | 5 | 5 | 5 | 5 | — |
| 11 | 1 | 5 | 5 | 5 | 5 | — |
|   | 0.3 | 4 | 4 | 5 | 5 | — |
| 12 | 1 | 5 | 5 | 5 | 5 | — |
|   | 0.3 | 5 | 4 | 5 | 5 | — |
| 13 | 1 | 5 | 5 | 5 | 5 | — |
|   | 0.3 | 5 | 4 | 5 | 5 | — |
| 14 | 1 | 5 | 5 | 5 | 5 | — |
|   | 0.3 | 4 | 5 | 5 | 5 | — |
| 15 | 1 | 5 | 4 | 5 | 5 | — |
|   | 0.3 | 5 | 4 | 5 | 3 | — |
| 16 | 1 | 3 | 4 | 5 | 5 | — |
|   | 0.3 | 3 | 3 | 5 | 5 | — |
| 17 | 1 | 3 | 4 | 5 | 5 | — |
|   | 0.3 | 3 | 2 | 5 | 5 | — |
| 18 | 1 | 5 | 5 | 5 | 5 | — |
|   | 0.3 | 5 | 4 | 5 | 5 | — |
| 19 | 1 | 5 | 4 | 5 | 5 | — |
|   | 0.3 | 5 | 2 | 5 | 5 | — |
| 20 | 1 | 5 | 5 | 5 | 5 | — |
|   | 0.3 | 5 | 3 | 5 | 5 | — |
| 21 | 1 | 5 | 5 | 5 | 5 | — |
|   | 0.3 | 5 | 4 | 5 | 5 | — |
| 22 | 1 | 5 | 4 | 5 | 5 | — |
|   | 0.3 | 3 | 1 | 4 | 5 | — |
| 23 | 1 | 5 | 5 | 5 | 5 | — |
|   | 0.3 | 5 | 4 | 5 | 5 | — |
| 24 | 1 | 5 | 4 | 5 | 5 | — |
|   | 0.3 | 4 | 3 | 4 | 5 | — |
| 25 | 1 | 5 | 3 | 5 | 5 | — |
|   | 0.3 | 4 | 2 | 5 | 4 | — |
| 28 | 1 | 5 | 5 | 5 | 5 | — |
|   | 0.3 | 5 | 3 | 5 | 5 | — |
| 29 | 1 | 5 | 4 | 5 | 5 | — |
|   | 0.3 | 5 | 2 | 5 | 5 | — |
| 30 | 1 | 5 | 5 | 5 | 5 | — |
|   | 0.3 | 5 | 3 | 5 | 5 | — |
| 31 | 1 | 5 | 4 | 5 | 5 | — |
|   | 0.3 | 5 | 3 | 5 | 5 | — |
| 32 | 1 | 5 | 1 | 4 | 5 | — |
|   | 0.3 | 4 | 0 | 2 | 4 | — |
| 33 | 1 | 5 | 3 | 5 | 5 | — |
|   | 0.3 | 5 | 2 | 4 | 5 | — |
| 34 | 1 | 4 | 2 | 4 | 5 | — |
|   | 0.3 | 4 | 1 | 4 | 5 | — |
| 35 | 1 | 5 | 5 | 5 | 5 | — |
|   | 0.3 | 5 | 3 | 5 | 5 | — |
| 36 | 1 | 4 | 3 | 5 | 5 | — |
|   | 0.3 | 4 | 0 | 3 | 4 | — |
| 37 | 1 | 5 | 5 | 5 | 5 | — |
|   | 0.3 | 2 | 3 | 4 | 4 | — |
| 38 | 1 | 5 | 5 | 5 | 5 | — |
|   | 0.3 | 3 | 2 | 3 | 5 | — |
| Simetryn | 1 | 5 | 4 | 5 | 5 | — |
|   | 0.3 | 3 | 2 | 5 | 4 | — |

TEST EXAMPLE 3

Test for soil treatment in an upland farm:

Upland farm soil was sieved and filled in polyethylene vats having an area of 1,000 cm². Seeds of various weeds and crops were sown and covered with the soil to a depth of 1 cm. After the sowing, a predetermined amount of a wettable powder of each of the compounds of this invention was sprayed onto the surface of the soil at a rate of 1000 liters as the amount of water per 10 hectare.

Twenty days after the treatment, the herbicidal effects of the test compounds on the weeds and the degrees of phytotoxicity of these compounds to the crops were examined, and evaluated as in Test Examples 1 and 2. The results are shown in Table 4.

In Tables 4 to 7, the following abbreviations were used to show the weeds.

E: fingergrass
F: green foxtail
G: *Cyperus microiria*
H: redroot pigweed
I: Polygonum sp.
J: jimsonweed
K: *Chenopodium serotinum*

TABLE 4

| Compd. No. | Rate of application (kg/ha) a.i. | Phytotoxicity | | | | Herbicidal effect | | | | | | |
|---|---|---|---|---|---|---|---|---|---|---|---|---|
| | | Corn | Wheat | Soybean | Cotton | E | F | G | H | I | J | K |
| 2 | 0.5 | — | + | ± | — | 5 | 5 | 5 | 5 | 5 | 5 | 5 |
| | 0.25 | — | — | — | — | 5 | 5 | 5 | 5 | 5 | 5 | 5 |
| 3 | 0.5 | — | + | ± | — | 5 | 5 | 5 | 5 | 5 | 5 | 5 |
| | 0.25 | — | — | — | — | 4 | 5 | 5 | 5 | 5 | 3 | 5 |
| 4 | 0.5 | — | ± | ± | — | 5 | 5 | 5 | 5 | 5 | 5 | 5 |
| | 0.25 | — | — | — | — | 3 | 5 | 5 | 5 | 4 | 4 | 5 |
| 7 | 0.5 | — | ± | ± | — | 5 | 5 | 5 | 5 | 5 | 5 | 5 |
| | 0.25 | — | — | — | — | 3 | 4 | 3 | 5 | 4 | 4 | 4 |
| 8 | 0.5 | — | ± | ± | — | 5 | 5 | 4 | 5 | 5 | 5 | 5 |
| | 0.25 | — | — | — | — | 4 | 3 | 4 | 5 | 5 | 5 | 5 |
| 9 | 0.5 | — | — | — | — | 5 | 5 | 5 | 5 | 5 | 5 | 5 |
| | 0.25 | — | — | — | — | 5 | 3 | 4 | 5 | 5 | 3 | 5 |
| 10 | 0.5 | — | ± | ± | — | 5 | 5 | 5 | 5 | 5 | 5 | 5 |
| | 0.25 | — | — | — | — | 5 | 5 | 5 | 5 | 5 | 5 | 5 |
| 11 | 0.5 | — | ± | ± | — | 5 | 5 | 5 | 5 | 5 | 5 | 5 |
| | 0.25 | — | — | — | — | 5 | 5 | 5 | 5 | 5 | 5 | 5 |
| 12 | 0.5 | — | ± | ± | — | 5 | 5 | 5 | 5 | 5 | 5 | 5 |
| | 0.25 | — | — | — | — | 5 | 5 | 5 | 5 | 5 | 4 | 5 |
| 13 | 0.5 | — | ± | ± | — | 5 | 5 | 5 | 5 | 5 | 5 | 5 |
| | 0.25 | — | — | — | — | 5 | 5 | 5 | 5 | 5 | 5 | 5 |
| 15 | 0.5 | — | ± | ± | — | 5 | 5 | 5 | 5 | 5 | 5 | 5 |
| | 0.25 | — | — | — | — | 5 | 4 | 5 | 4 | 4 | 3 | 4 |
| 18 | 0.5 | — | ± | ± | — | 5 | 5 | 5 | 5 | 5 | 5 | 5 |
| | 0.25 | — | — | — | — | 5 | 4 | 5 | 5 | 5 | 5 | 5 |
| 19 | 0.5 | — | ± | ± | — | 5 | 5 | 5 | 5 | 5 | 5 | 5 |
| | 0.25 | — | — | — | — | 5 | 5 | 5 | 5 | 5 | 5 | 5 |
| 20 | 0.5 | — | ± | ± | — | 5 | 5 | 5 | 5 | 5 | 5 | 5 |
| | 0.25 | — | — | — | — | 5 | 3 | 5 | 4 | 5 | 5 | 5 |
| 21 | 0.5 | — | ± | ± | — | 5 | 5 | 5 | 5 | 5 | 5 | 5 |
| | 0.25 | — | — | — | — | 5 | 3 | 5 | 5 | 5 | 4 | 5 |
| 22 | 0.5 | — | ± | ± | — | 5 | 5 | 5 | 5 | 5 | 5 | 5 |
| | 0.25 | — | — | — | — | 5 | 5 | 5 | 5 | 5 | 5 | 5 |
| 23 | 0.5 | — | ± | ± | — | 5 | 5 | 5 | 5 | 5 | 5 | 5 |
| | 0.25 | — | — | — | — | 5 | 4 | 5 | 5 | 5 | 4 | 5 |
| 24 | 0.5 | — | — | — | — | 5 | 5 | 5 | 5 | 5 | 3 | 5 |
| | 0.25 | — | — | — | — | 5 | 4 | 4 | 5 | 5 | 3 | 3 |
| 25 | 0.5 | — | — | — | — | 5 | 4 | 4 | 5 | 5 | 2 | 3 |
| | 0.25 | — | — | — | — | 3 | 3 | 3 | 4 | 2 | 1 | 3 |
| 26 | 0.5 | — | — | — | — | 5 | 5 | 4 | 5 | 5 | 5 | 5 |
| | 0.25 | — | — | — | — | 3 | 3 | 3 | 5 | 4 | 3 | 5 |
| 27 | 0.5 | — | — | — | — | 5 | 5 | 5 | 5 | 5 | 5 | 5 |
| | 0.25 | — | — | — | — | 3 | 2 | 4 | 5 | 4 | 4 | 5 |
| 29 | 0.5 | — | ± | ± | — | 5 | 4 | 5 | 5 | 5 | 5 | 5 |
| | 0.25 | — | — | — | — | 4 | 3 | 5 | 5 | 5 | 5 | 5 |
| 30 | 0.5 | — | ± | ± | — | 5 | 5 | 5 | 5 | 5 | 5 | 5 |
| | 0.25 | — | — | — | — | 5 | 4 | 5 | 5 | 5 | 5 | 5 |
| 31 | 0.5 | — | ± | ± | — | 5 | 5 | 5 | 5 | 5 | 5 | 5 |
| | 0.25 | — | — | — | — | 5 | 3 | 4 | 5 | 5 | 5 | 5 |
| 33 | 0.5 | — | — | — | — | 5 | 5 | 5 | 5 | 5 | 5 | 5 |
| | 0.25 | — | — | — | — | 3 | 3 | 3 | 4 | 3 | 4 | 4 |
| 34 | 0.5 | — | — | — | — | 5 | 5 | 5 | 5 | 5 | 5 | 5 |
| | 0.25 | — | — | — | — | 3 | 3 | 4 | 4 | 4 | 4 | 4 |
| 35 | 0.5 | — | ± | ± | — | 5 | 5 | 5 | 5 | 5 | 5 | 5 |
| | 0.25 | — | — | — | — | 5 | 3 | 4 | 4 | 4 | 3 | 4 |
| 37 | 0.5 | — | — | — | — | 5 | 5 | 5 | 5 | 5 | 5 | 5 |
| | 0.25 | — | — | — | — | 3 | 3 | 4 | 4 | 4 | 3 | 5 |
| Atrazine | 0.5 | — | ++ | × | + | 4 | 3 | 5 | 5 | 5 | 5 | 5 |
| | 0.25 | — | + | +++ | — | 3 | 2 | 4 | 5 | 5 | 5 | 5 |
| Ametryn | 0.5 | — | + | + | — | 5 | 5 | 5 | 5 | 4 | 5 | 5 |
| | 0.25 | — | — | — | — | 5 | 1 | 4 | 5 | 3 | 0 | 5 |
| Simazine | 0.5 | + | + | ± | ± | 1 | 1 | 2 | 2 | 0 | 0 | 3 |
| | 0.25 | — | — | — | — | 0 | 0 | 0 | 2 | 0 | 0 | 1 |

TEST EXAMPLE 4

Test for foliar treatment in an upland farm:
Test Example 3 was repeated except that the treatment was carried out 14 days after the sowing. The test results are shown in Table 5.

In Tables 5 to 7, L and M indicate the following weeds.
L: oat
M: velvetleaf

TABLE 5

| Compd. No. | Rate of application (kg/ha) a.i. | E | F | L | G | H | I | J | K | M | Corn |
|---|---|---|---|---|---|---|---|---|---|---|---|
| 1 | 0.5 | 5 | 5 | 5 | 5 | 5 | 5 | 5 | 5 | 5 | — |
|   | 0.25 | 5 | 4 | 4 | 3 | 5 | 5 | 4 | 4 | 5 | — |
| 2 | 0.5 | 5 | 5 | 5 | 5 | 5 | 5 | 5 | 5 | 5 | ± |
|   | 0.25 | 5 | 5 | 5 | 5 | 5 | 5 | 5 | 5 | 5 | — |
| 3 | 0.5 | 5 | 5 | 5 | 5 | 5 | 5 | 5 | 5 | 5 | ± |
|   | 0.25 | 5 | 5 | 5 | 5 | 5 | 5 | 5 | 5 | 5 | — |
| 4 | 0.5 | 5 | 5 | 5 | 5 | 5 | 5 | 5 | 5 | 5 | ± |
|   | 0.25 | 4 | 4 | 5 | 3 | 5 | 5 | 5 | 5 | 5 | — |
| 7 | 0.5 | 5 | 5 | 5 | 5 | 5 | 5 | 5 | 5 | 5 | — |
|   | 0.25 | 5 | 5 | 4 | 5 | 5 | 5 | 5 | 5 | 5 | — |
| 8 | 0.5 | 5 | 5 | 5 | 5 | 5 | 5 | 5 | 5 | 5 | — |
|   | 0.25 | 5 | 5 | 4 | 5 | 5 | 5 | 5 | 5 | 5 | — |
| 9 | 0.5 | 5 | 5 | 3 | 4 | 5 | 5 | 5 | 5 | 5 | — |
|   | 0.25 | 5 | 3 | 2 | 3 | 5 | 5 | 3 | 5 | 4 | — |
| 10 | 0.5 | 4 | 4 | 4 | 5 | 5 | 5 | 5 | 5 | 5 | — |
|   | 0.25 | 3 | 3 | 3 | 5 | 5 | 5 | 5 | 5 | 5 | — |
| 11 | 0.5 | 5 | 5 | 5 | 5 | 5 | 5 | 5 | 5 | 5 | — |
|   | 0.25 | 5 | 5 | 5 | 5 | 5 | 5 | 5 | 5 | 5 | — |
| 12 | 0.5 | 5 | 5 | 5 | 5 | 5 | 5 | 5 | 5 | 5 | — |
|   | 0.25 | 5 | 5 | 5 | 5 | 5 | 5 | 5 | 5 | 5 | — |
| 13 | 0.5 | 5 | 5 | 5 | 5 | 5 | 5 | 5 | 5 | 5 | — |
|   | 0.25 | 5 | 5 | 5 | 5 | 5 | 5 | 5 | 5 | 5 | — |
| 15 | 0.5 | 5 | 4 | 3 | 4 | 5 | 5 | 5 | 5 | 5 | — |
|   | 0.25 | 3 | 3 | 2 | 3 | 4 | 4 | 3 | 4 | 4 | — |
| 16 | 0.5 | 5 | 5 | 5 | 5 | 5 | 5 | 5 | 5 | 5 | — |
|   | 0.25 | 5 | 4 | 3 | 3 | 5 | 4 | 3 | 4 | 5 | — |
| 17 | 0.5 | 5 | 5 | 5 | 5 | 5 | 5 | 5 | 5 | 5 | — |
|   | 0.25 | 3 | 3 | 3 | 4 | 5 | 5 | 5 | 5 | 4 | — |
| 18 | 0.5 | 5 | 5 | 5 | 5 | 5 | 5 | 5 | 5 | 5 | — |
|   | 0.25 | 5 | 5 | 5 | 5 | 5 | 5 | 5 | 5 | 5 | — |
| 19 | 0.5 | 5 | 5 | 5 | 5 | 5 | 5 | 5 | 5 | 5 | — |
|   | 0.25 | 5 | 5 | 5 | 5 | 5 | 5 | 5 | 5 | 5 | — |
| 20 | 0.5 | 5 | 5 | 5 | 5 | 5 | 5 | 5 | 5 | 5 | — |
|   | 0.25 | 5 | 5 | 5 | 5 | 5 | 5 | 5 | 5 | 5 | — |
| 21 | 0.5 | 5 | 5 | 5 | 5 | 5 | 5 | 5 | 5 | 5 | — |
|   | 0.25 | 5 | 5 | 5 | 5 | 5 | 5 | 5 | 5 | 5 | — |
| 22 | 0.5 | 5 | 5 | 5 | 5 | 5 | 5 | 5 | 5 | 5 | — |
|   | 0.25 | 5 | 4 | 3 | 5 | 5 | 5 | 5 | 5 | 5 | — |
| 23 | 0.5 | 5 | 5 | 5 | 5 | 5 | 5 | 5 | 5 | 5 | — |
|   | 0.25 | 4 | 4 | 3 | 5 | 5 | 5 | 5 | 5 | 5 | — |
| 24 | 0.5 | 4 | 4 | 4 | 5 | 5 | 5 | 5 | 5 | 5 | — |
|   | 0.25 | 3 | 4 | 2 | 4 | 4 | 5 | 5 | 5 | 5 | — |
| 25 | 0.5 | 3 | 3 | 4 | 4 | 5 | 5 | 5 | 5 | 5 | — |
|   | 0.25 | 3 | 3 | 2 | 3 | 4 | 5 | 5 | 5 | 5 | — |
| 26 | 0.5 | 2 | 2 | 2 | 3 | 5 | 5 | 5 | 5 | 5 | — |
|   | 0.25 | 1 | 2 | 0 | 3 | 5 | 5 | 5 | 4 | 5 | — |
| 27 | 0.5 | 5 | 3 | 3 | 3 | 3 | 5 | 5 | 5 | 5 | — |
|   | 0.25 | 2 | 3 | 2 | 3 | 5 | 5 | 3 | 4 | 5 | — |
| 28 | 0.5 | 4 | 3 | 5 | 4 | 5 | 5 | 5 | 5 | 5 | — |
|   | 0.25 | 2 | 2 | 3 | 4 | 5 | 5 | 5 | 3 | 5 | — |
| 29 | 0.5 | 5 | 5 | 5 | 5 | 5 | 5 | 5 | 5 | 5 | — |
|   | 0.25 | 5 | 5 | 5 | 5 | 5 | 5 | 5 | 5 | 5 | — |
| 30 | 0.5 | 5 | 5 | 5 | 5 | 5 | 5 | 5 | 5 | 5 | — |
|   | 0.25 | 5 | 5 | 5 | 5 | 5 | 5 | 5 | 5 | 5 | — |
| 31 | 0.5 | 4 | 4 | 5 | 4 | 5 | 5 | 5 | 5 | 5 | — |
|   | 0.25 | 2 | 3 | 3 | 3 | 3 | 5 | 5 | 4 | 5 | — |
| 32 | 0.5 | 3 | 3 | 4 | 3 | 5 | 5 | 5 | 5 | 5 | — |
|   | 0.25 | 2 | 3 | 2 | 3 | 3 | 5 | 5 | 3 | 5 | — |
| 33 | 0.5 | 5 | 5 | 5 | 5 | 5 | 5 | 5 | 5 | 5 | — |
|   | 0.25 | 5 | 5 | 5 | 5 | 5 | 5 | 5 | 5 | 5 | — |
| 34 | 0.5 | 5 | 5 | 5 | 5 | 5 | 5 | 5 | 5 | 5 | — |
|   | 0.25 | 5 | 5 | 4 | 5 | 5 | 5 | 5 | 5 | 5 | — |
| 35 | 0.5 | 4 | 3 | 5 | 4 | 5 | 5 | 5 | 5 | 5 | — |
|   | 0.25 | 2 | 3 | 4 | 4 | 4 | 5 | 5 | 3 | 5 | — |
| 36 | 0.5 | 4 | 3 | 4 | 4 | 5 | 5 | 5 | 4 | 5 | — |
|   | 0.25 | 2 | 3 | 3 | 4 | 3 | 3 | 5 | 3 | 4 | — |
| 37 | 0.5 | 4 | 3 | 3 | 4 | 5 | 5 | 5 | 5 | 5 | — |
|   | 0.25 | 3 | 3 | 2 | 3 | 4 | 5 | 5 | 4 | 5 | — |
| 38 | 0.5 | 5 | 5 | 5 | 5 | 5 | 5 | 5 | 5 | 5 | — |
|   | 0.25 | 5 | 4 | 5 | 4 | 5 | 5 | 5 | 5 | 5 | — |
| 39 | 0.5 | 4 | 3 | 4 | 3 | 4 | 5 | 5 | 5 | 5 | — |
|   | 0.25 | 3 | 2 | 2 | 3 | 3 | 5 | 5 | 3 | 3 | — |
| Atrazine | 0.5 | 2 | 2 | 3 | 5 | 5 | 5 | 5 | 5 | 3 | — |
|   | 0.25 | 1 | 1 | 2 | 3 | 5 | 5 | 5 | 5 | 0 | — |
| Simazine | 0.5 | 0 | 0 | 0 | 0 | 0 | 1 | 2 | 2 | 1 | — |
|   | 0.25 | 0 | 0 | 0 | 0 | 0 | 1 | 0 | 0 | 0 | — |

TEST EXAMPLE 5

Test for soil treatment in an upland farm:
Upland farm soil was sieved and filled in plastic vats having an area of 1,000 cm². Seeds of various weeds and crops were sown and covered with the soil to a depth of 1 cm. After the sowing, a predetermined amount of a wettable powder of each of the test compounds was sprayed onto the surface of the soil at a rate of 1000 liters as the amount of water per hectare.

Twenty days after the treatment, the herbicidal effects of the test compounds on the weeds and the degrees of phytotoxicity of these compounds to the crops were examined, and evaluated as in Test Example 1. The results are shown in Table 6.

Comparative compounds Nos. 1 to 3 shown in Table 6 were as follows:

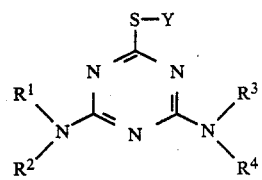

| Comparative compound No. | Y | $R^1$ | $R^2$ | $R^3$ | $R^4$ | Physical constant |
|---|---|---|---|---|---|---|
| 1 | $CHF_2$ | Et | H | iso-Pr | H | m.p. 59–61° C. |
| 2 | $CHF_2$ | Me | H | iso-Pr | H | m.p. 62–63° C. |
| 3 | $CHF_2$ | iso-Pr | H | iso-Pr | H | m.p. 57–58° C. |

In Tables 6 and 7, N, O, P and Q indicate the following weeds.
N: wild oat
O: lamb's quarters
P: tall morningglory
Q: cocklebur

TABLE 6

| Compd. No. | Rate of application (kg/ha) a.i. | Herbicidal effect | | | | | | | | | | | Phytotoxicity | |
|---|---|---|---|---|---|---|---|---|---|---|---|---|---|---|
| | | A | E | F | N | G | H | I | O | P | M | Q | Corn | Cotton |
| 10 | 0.25 | 5 | 5 | 5 | 4 | 5 | 5 | 5 | 5 | 5 | 5 | 3 | — | ± |
| | 0.125 | 3.5 | 5 | 3.5 | 1 | 4.5 | 4.5 | 3.5 | 5 | 1 | 1 | 0 | — | — |
| | 0.0625 | 2.5 | 5 | 3 | 0 | 4 | 4 | 3.5 | 5 | 0 | 0 | 0 | — | — |
| 18 | 0.25 | 4.5 | 5 | 4 | 1 | 5 | 5 | 5 | 5 | 5 | 5 | 2 | ± | — |
| | 0.125 | 3.5 | 5 | 3 | 0 | 5 | 5 | 4 | 5 | 4 | 3 | 0 | — | — |
| | 0.0625 | 1 | 2 | 0 | 0 | 4.5 | 5 | 1 | 5 | 1 | 0 | 0 | — | — |
| 19 | 0.25 | 4.5 | 5 | 5 | 3.5 | 5 | 5 | 5 | 5 | 5 | 5 | 1 | — | — |
| | 0.125 | 3.5 | 5 | 4.5 | 1 | 3.5 | 5 | 5 | 3.5 | 2 | 3.5 | 0 | — | — |
| | 0.0625 | 1 | 5 | 2 | 0 | 1 | 5 | 4 | 1 | 0 | 2 | 0 | — | — |
| Comp. No. 1 | 0.25 | 3.5 | 5 | 4.5 | 1 | 5 | 5 | 5 | 5 | 1 | 3 | 1 | ± | — |
| | 0.125 | 1 | 5 | 1 | 0 | 3 | 5 | 3.5 | 5 | 0 | 1 | 0 | — | — |
| | 0.0625 | 0 | 3 | 0 | 0 | 3 | 3.5 | 2.5 | 4.5 | 0 | 0 | 0 | — | — |
| Comp. No. 2 | 0.25 | 2 | 5 | 5 | 2 | 5 | 5 | 4 | 5 | 0 | 1 | 0 | — | — |
| | 0.125 | 0 | 4 | 2 | 0 | 5 | 5 | 2 | 2 | 0 | 0 | 0 | — | — |
| | 0.0625 | 0 | 1 | 0 | 0 | 1 | 1 | 0 | 0 | 0 | 0 | 0 | — | — |
| Comp. No. 3 | 0.25 | 2 | 5 | 3.5 | 1 | 5 | 5 | 4 | 5 | 0 | 1 | 0 | — | — |
| | 0.125 | 1 | 2 | 2 | 0 | 1 | 4.5 | 2 | 2 | 0 | 1 | 0 | — | — |
| | 0.0625 | 0 | 0 | 0 | 0 | 0 | 2 | 0 | 0 | 0 | 0 | 0 | — | — |
| Atrazine | 0.25 | 2 | 2.5 | 2 | 3 | 4.5 | 5 | 5 | 5 | 2 | 1 | 0 | — | ± |
| | 0.125 | 1 | 2 | 1 | 2 | 3.5 | 4.5 | 4 | 5 | 0 | 0 | 0 | — | — |
| | 0.0625 | 0 | 0 | 0 | 2 | 2 | 1 | 1 | 5 | 0 | 0 | 0 | — | — |
| Non-treated | | 0 | 0 | 0 | 0 | 0 | 0 | 0 | 0 | 0 | 0 | 0 | — | — |

TEST EXAMPLE 6

A field test in an upland farm:

Corn was sown in rows spaced 50 cm apart in an upland farm, and soil containing seeds of weeds were scattered throughout the field. After the sowing, test areas each having an area of 10 m² (5 m×2 m) were set up, and a predetermined amount of an emulsifiable concentrate of each of the test compounds was sprayed onto the surface of the soil at a rate of 300 liters as the amount of water per hectare.

Forty-seven days after the treatment, the herbicidal effects of the test compounds and their degrees of phytotoxicity to the crop were examined. The results are shown in Table 7.

The herbicidal effects were evaluated by the herbicidal rate (percent) based on the non-treated area which ranges from 0% to 100% (withered). The phytotoxicity to the crop was evaluated by the phytotoxicity rate (percent) which ranges from 0% (no phytotoxicity) to 100% (withered).

Comparative compound No. 1 in Table 7 was the same as in Test Example 5. Cyanazin is 2-(2-chloro-4-ethylamino S-triazine 6-yl amino)2-methylpropionitrile.

In Table 7 and other tables, R, S and T indicate the following weeds.
R: Johnson grass
S: wild mustard
T: *Acalypha australis*

TABLE 7

| Compd. No. | Rate of application (kg/ha) a.i. | Herbicidal effect | | | | | | | | | | | | | Phytotoxicity |
|---|---|---|---|---|---|---|---|---|---|---|---|---|---|---|---|
| | | A | E | F | R | H | I | O | J | S | T | M | P | Q | Corn |
| 10 | 1 | 93 | 93 | 95 | 70 | 100 | 100 | 100 | 100 | 98 | 100 | 100 | 100 | 100 | 5 |
| | 0.5 | 55 | 75 | 70 | 10 | 88 | 100 | 80 | 95 | 60 | 10 | 40 | | | 0 |
| Comp. No. 1 | 1 | 98 | 93 | 95 | 30 | 100 | 100 | 100 | 78 | 98 | 100 | 75 | 30 | 0 | 5 |
| | 0.5 | 55 | 75 | 83 | 45 | 95 | 100 | 100 | 75 | 75 | 98 | 20 | 0 | 10 | 0 |
| Cyanazine | 2 | 90 | 95 | 100 | 10 | 95 | 100 | 100 | 100 | 95 | 100 | 55 | 75 | 100 | 5 |
| | 1 | 90 | 75 | 95 | 25 | 93 | 100 | 100 | 65 | 100 | 98 | 45 | 60 | 50 | 0 |
| Non-treated | | 0 | 0 | 0 | 0 | 0 | 0 | 0 | 0 | 0 | 0 | 0 | 0 | 0 | 0 |

TEST EXAMPLE 7

Test for combination treatment in an upland farm by soil treatment:

Upland farm soil was sieved and filled in plastic vats having an area of 1,000 cm². Seeds of various weeds and crops were sown and covered with the soil to a depth of 1 cm. After the sowing, a predetermined amount of a wettable powder of each of the test compounds including combination with the commercial formulations of atrazine was sprayed onto the surface of the soil at a rate of 500 liters as the amount of water per hectare.

Twenty days after the treatment, the herbicidal effects of the test compounds on the weeds and the degrees of phytotoxicity of these compounds to the crops were examined, and evaluated as in Test Example 6. The results are shown in Table 8.

In Table 8, U indicates the following weed.
U: common ragweed (*Ambrosia artemisiifolia*)

TABLE 8

| Compound No. | Rate of application (kg ai/ha) | Herbicidal effect | | | | | | | | | Phytotoxicity | |
|---|---|---|---|---|---|---|---|---|---|---|---|---|
| | | A | E | F | O | M | U | H | J | P | Corn | Cotton |
| 10 | 0.5 | 100 | 100 | 100 | 100 | 100 | 100 | 100 | 100 | 100 | 45 | 0 |

TABLE 8-continued

| Compound No. | Rate of application (kg ai/ha) | Herbicidal effect | | | | | | | | | Phytotoxicity | |
|---|---|---|---|---|---|---|---|---|---|---|---|---|
| | | A | E | F | O | M | U | H | J | P | Corn | Cotton |
| | 0.25 | 100 | 100 | 100 | 100 | 100 | 100 | 100 | 100 | 60 | 0 | 0 |
| Atrazine | 0.5 | 50 | 30 | 55 | 100 | 80 | 95 | 100 | 100 | 75 | 0 | 0 |
| | 0.25 | 30 | 25 | 70 | 100 | 15 | 90 | 100 | 80 | 65 | 0 | 0 |
| Cyanazine | 0.5 | 10 | 100 | 100 | 100 | 80 | 100 | 95 | 45 | 60 | 0 | 0 |
| | 0.25 | 0 | 90 | 50 | 100 | 35 | 55 | 90 | 25 | 0 | 0 | 0 |
| 10 | 0.5(0.25 + 0.25) | 40 | 100 | 100 | 100 | 100 | 100 | 100 | 100 | 75 | 10 | 0 |
| + | 0.5(0.17 + 0.33) | 60 | 100 | 100 | 100 | 100 | 100 | 100 | 100 | 90 | 10 | 0 |
| Atrazine | 0.5(0.125 + 0.375) | 65 | 100 | 50 | 100 | 90 | 100 | 100 | 100 | 100 | 0 | 0 |
| (*) | 0.5(0.1 + 0.4) | 40 | 95 | 80 | 100 | 100 | 100 | 100 | 100 | 95 | 0 | 0 |
| Atrazine | 0.5(0.25 + 0.25) | 0 | 40 | 40 | 100 | 100 | 95 | 100 | 70 | 50 | 0 | 0 |
| + | 0.5(0.17 + 0.33) | 20 | 100 | 80 | 100 | 55 | 90 | 95 | 90 | 0 | 0 | 0 |
| Cyanazine | 0.5(0.125 + 0.375) | 10 | 95 | 80 | 100 | 60 | 100 | 85 | 95 | 10 | 0 | 0 |
| (*) | | | | | | | | | | | | |
| Non-treated | | 0 | 0 | 0 | 0 | 0 | 0 | 0 | 0 | 0 | 0 | 0 |

(*): The parenthesized figures show the amounts of the ingredients of the mixture.

TEST EXAMPLE 8

Test for a herbicidal spectrum in an upland farm by soil treatment:

Upland farm soil was sieved and filled in plastic vats having an area of 1,000 cm². Seeds of various weeds were sown (8 to 9 species of weeds per pot) and covered with the soil to a depth of 1 cm. After the sowing, a predetermined amount of a wettable powder of each of the test compounds was sprayed onto the surface of the soil at a rate of 1000 liters as the amount of water per hectare.

Twenty-five days after the treatment, the herbicidal effects of the test compounds on the weeds were examined. The results are shown in Table 9.

The herbicidal effects were evaluated on a scale of 0 to 10 where 10 indicates a herbicidal rate of 100% (withered) based on the non-treated area, and 0, a herbicidal rate of 0% based on the non-treated area.

In Table 9, V, W, X, Y and Z indicate the following weeds.

V: goosegrass (*Eleusine indica*)
W: common purslane
X: blackjack (*Bidens pilosa*)
Y: sunflower
Z: white-bird's-eye

Soil surface treatment

Upland farm soil was sieved and filled in plasic vats having an area of 1,000 cm² and a height of 9 cm. Seeds of various weeds were sown and covered with soil to a depth of 1 cm. After the sowing, a predetermined amount of a wettable powder of each of the test compounds was sprayed onto the soil surface at a rate of 1000 liters as the amount of water per hectare.

Soil incorporation treatment

A predetermined amount of a wettable powder of each of the test compounds was sprayed onto the sieved upland farm soil at a rate of 1000 liters, as the amount of water, per hectare, and mixed well with the soil. The soil was then immediately filled in plastic vats each having an area of 1,000 cm² and a height of 9 cm, and seeds of various weeds were sown and covered with the soil to a depth of 1 cm.

Twenty days after the treatment in each of the above cases, the herbicidal effects of the compounds on the weeds were examined and evaluated as in Test Example 8. The results are shown in Table 10.

TABLE 9

| Compd. No. Rate of application (kg/ha, ai) | | 10 (invention) | | | No. 1 (comparison) | | | Atrazine | | | Non-treated |
|---|---|---|---|---|---|---|---|---|---|---|---|
| | | 0.5 | 0.25 | 0.125 | 0.5 | 0.25 | 0.125 | 1 | 0.5 | 0.25 | |
| Narrow-leaved weeds | A | 100 | 100 | 70 | 100 | 100 | 50 | 90 | 70 | 40 | 0 |
| | E | 100 | 100 | 100 | 100 | 100 | 95 | 80 | 30 | 0 | 0 |
| | F | 100 | 85 | 70 | 100 | 100 | 30 | 60 | 40 | 0 | 0 |
| | N | 70 | 50 | 10 | 0 | 0 | 0 | 90 | 50 | 0 | 0 |
| | V | 100 | 100 | 85 | 90 | 90 | 20 | 90 | 80 | 10 | 0 |
| | G | 100 | 100 | 100 | 95 | 78 | 30 | 100 | 100 | 100 | 0 |
| Broad-leaved weeds | W | 100 | 100 | 100 | 100 | 100 | 100 | 100 | 100 | 100 | 0 |
| | H | 100 | 100 | 100 | 100 | 100 | 95 | 100 | 100 | 100 | 0 |
| | X | 100 | 100 | 100 | 100 | 50 | 0 | 100 | 90 | 60 | 0 |
| | Y | 80 | 20 | 10 | 0 | 0 | 0 | 100 | 35 | 15 | 0 |
| | M | 100 | 70 | 10 | 100 | 50 | 20 | 100 | 50 | 10 | 0 |
| | O | 100 | 100 | 100 | 100 | 95 | 95 | 100 | 100 | 97 | 0 |
| | S | 100 | 90 | 60 | 97 | 80 | 30 | 100 | 100 | 65 | 0 |
| | P | 100 | 70 | 60 | 80 | 20 | 0 | 95 | 70 | 40 | 0 |
| | T | 100 | 100 | 95 | 100 | 100 | 40 | 100 | 100 | 100 | 0 |
| | Z | 100 | 100 | 95 | 100 | 100 | 85 | 100 | 100 | 100 | 0 |

TEST EXAMPLE 9

Test for soil surface treatment and soil incorporation treatment in an upland farm:

TABLE 10

| Compd. No. | Treating method | Rate of application (kg/ha, ai) | E | F | R | M | P | Y |
|---|---|---|---|---|---|---|---|---|
| 10 | Soil surface | 0.5 | 100 | 100 | 75 | 100 | 80 | 75 |
| | | 0.25 | 95 | 75 | 0 | 70 | 50 | 40 |

TABLE 10-continued

| Compd. No. | Treating method | Rate of application (kg/ha, ai) | E | F | R | M | P | Y |
|---|---|---|---|---|---|---|---|---|
| | | 0.125 | 80 | 60 | 0 | 20 | 0 | 0 |
| | Soil incorporation | 1 | 100 | 100 | 85 | 100 | 80 | 100 |
| | | 0.5 | 93 | 70 | 20 | 100 | 100 | 100 |
| | | 0.25 | 50 | 30 | 0 | 93 | 65 | 100 |
| Comp. No. 1 | Soil surface | 0.5 | 100 | 100 | 10 | 40 | 45 | 0 |
| | | 0.25 | 40 | 40 | 0 | 20 | 0 | 0 |
| | | 0.125 | 10 | 10 | 0 | 10 | 0 | 0 |
| | Soil incorporation | 2 | 100 | 93 | 10 | 100 | 90 | 10 |
| | | 1 | 95 | 30 | 0 | 95 | 60 | 0 |
| | | 0.5 | 20 | 20 | 0 | 65 | 20 | 0 |
| Non-treated | | | 0 | 0 | 0 | 0 | 0 | 0 |

FORMULATION EXAMPLE 1

Granules:

Five parts of compound No. 1, 50 parts of bentonite, 40 parts of talc, 2 parts of sodium dodecylbenzenesulfonate, 2 parts of sodium ligninsulfonate and 1 part of polyoxyethylenealkyl aryl ether were mixed, and kneaded with a suitable amount of water. The kneaded mixture was granulated by means of a granulator to obtain 100 parts of granules.

Granules were prepared by the same method as above using compounds Nos. 2 to 44, respectively.

FORMULATION EXAMPLE 2

Wettable powder:

Twenty parts of compound No. 1, 60 parts of diatomaceous earth, 15 parts of white carbon, 3 parts of sodium ligninsulfonate and 2 parts of sodium dodecylbenzenesulfonate were mixed and well pulverized in a kneader to obtain 100 parts of a wettable powder.

Wettable powders were prepared in the same way as above using compounds Nos. 2 to 44, respectively.

FORMULATION EXAMPLE 3

Emulsifiable concentrate:

Compound No. 1 was dissolved in a mixture composed of 55 parts of xylene, 10 parts of cyclohexanone, 3 parts of calcium dodecylbenzenesulfonate and 2 parts of polyoxyethylene alkyl aryl ether to obtain 100 parts of an emulsifiable concentrate.

Emulsifiable concentrates were prepared in the same way as above using compounds Nos. 2 to 44, respectively.

What is claimed is:

1. A 1,3,5-triazine derivative represented by the following formula (I)'

$$\text{(I)'}$$

wherein $R^1$ and $R^3$, independently from each other, represent a group selected from the class consisting of linear or branched $C_1$-$C_6$ alkyl groups, $C_2$-$C_6$ alkenyl groups, $C_1$-$C_6$ alkyl groups substituted by $C_1$-$C_6$ alkoxy, $C_3$-$C_6$ cycloalkyl groups, a phenyl group unsubstituted or substituted by a substituent selected from halogen, nitro, cyano, lower alkyl, lower alkoxy, lower alkylthio and fluoro-substituted lower alkyl, and $C_7$-$C_9$ aralkyl groups unsubstituted or substituted by a substituent selected from halogen, nitro, cyano, lower alkyl, lower alkoxy, lower alkylthio and fluoro-substituted lower alkyl.

2. The 1,3,5-triazine derivative of claim 1 wherein $R^1$ is methyl, ethyl or propyl, $R^3$ is methyl, ethyl, propyl, cyclopropyl, butyl, $(CH_2)_3OCH_3$, $-CHC_2H_5$, $-CCH_3C_2H_5$, $-CH_2CH=CH_2$, $$-\overset{CH_3}{\underset{|}{CH}}-C_6H_5,$$

$(CH_2)_2OCH_3$, or $(CH_2)_2OC_2H_5$.

3. The 1,3,5-triazine derivative of claim 2 wherein at least one of $R^1$ and $R^3$ is said $C_2$-$C_6$ alkenyl, $C_3$-$C_6$ cycloalkyl, phenyl, substituted phenyl, $C_7$-$C_9$ aralkyl, or substituted $C_7$-$C_9$ aralkyl.

4. 2-Difluoromethoxy-4-ethylamino-6-isopropylamino-1,3,5-triazine.

5. A herbicidal composition comprising a herbicidally effective amount of, as an active ingredient, a 1,3,5-triazine derivative represented by the following formula (I)'

$$\text{(I)'}$$

wherein $R^1$ and $R^3$, independently from each other, represent a group selected from the class consisting of linear or branched $C_1$-$C_6$ alkyl groups, $C_2$-$C_6$ alkenyl groups, $C_1$-$C_6$ alkyl groups substituted by $C_1$-$C_6$ alkoxy, $C_3$-$C_6$ cycloalkyl groups, a phenyl group unsubstituted or substituted by a substituent selected from halogen, nitro, cyano, lower alkyl, lower alkoxy, lower alkylthio or fluoro-substituted lower alkyl, and $C_7$-$C_9$ aralkyl groups unsubstituted or substituted by a substituent selected from halogen, nitro, cyano, lower alkyl, lower alkoxy, lower alkylthio and fluoro-substituted lower alkyl, and an agriculturally acceptable diluent or carrier.

6. The herbicidal composition of claim 4 wherein the amount of the active ingredient is about 1 to 80% by weight based on the weight of the composition.

7. The herbicidal composition of claim 5 in which the 1,3,5-triazine derivative is 2-difluoromethoxy-4-ethylamino-6-isopropylamino-1,3,5-triazine.

8. A method of controlling the growth of undesired vegetation, which comprises applying an agriculturally effective amount of at least one compound of claim 2 to the locus of such vegetation.

9. The method of claim 6 wherein the time of application is before emergence of the undesired vegetation, and the locus is the soil and/or the soil surface where the vegetation is likely to occur.

10. The method of claim 8 wherein the rate of application, as the amount of the said at least one compound is about 0.015 to 10 kg/hectare.

* * * * *

UNITED STATES PATENT AND TRADEMARK OFFICE
CERTIFICATE OF CORRECTION

PATENT NO. : 4,816,064
DATED : March 28, 1989
INVENTOR(S) : KAZUHIKO KONNO, ET AL.

It is certified that error appears in the above-identified patent and that said Letters Patent is hereby corrected as shown below:

<u>IN THE CLAIMS</u>

Column 22, claim 3, line 18, delete "claim 2", insert --claim 1--;

claim 6, line 50, delete "claim 4", insert --claim 5--;

claim 9, line 60, delete "claim 6", insert --Claim 8--.

Signed and Sealed this

Fourteenth Day of November, 1989

Attest:

JEFFREY M. SAMUELS

*Attesting Officer*     *Acting Commissioner of Patents and Trademarks*